United States Patent [19]

Fuerst

[11] Patent Number: 4,651,752
[45] Date of Patent: Mar. 24, 1987

[54] BIOPSY NEEDLE

[76] Inventor: Erwin J. Fuerst, 1183 N. River Rd., St. Clair, Mich. 48079

[21] Appl. No.: 709,702

[22] Filed: Mar. 8, 1985

[51] Int. Cl.[4] ............................................. A61B 17/34
[52] U.S. Cl. ...................................... 128/754; 128/309
[58] Field of Search ............................... 128/305–318, 128/749–754, 757, 758

[56] References Cited

U.S. PATENT DOCUMENTS

| | | | |
|---|---|---|---|
| 737,293 | 8/1903 | Summerfeldt | 128/751 |
| 1,339,691 | 5/1920 | Diamant | 128/309 |
| 1,545,761 | 7/1925 | Gurtov | 128/309 |
| 1,564,356 | 12/1925 | Kelley | 128/309 |
| 2,729,210 | 1/1956 | Spencer | 128/751 |
| 3,001,522 | 9/1961 | Silverman | 128/754 |
| 3,007,471 | 11/1961 | McClure | 128/754 |
| 3,407,815 | 10/1968 | Abelson | 128/309 |
| 3,844,272 | 10/1974 | Banko | 128/305 |
| 3,915,169 | 10/1975 | McGuire | 128/305 |
| 4,282,884 | 8/1981 | Boebel | 128/754 |

FOREIGN PATENT DOCUMENTS

| | | | |
|---|---|---|---|
| 2823572 | 12/1978 | Fed. Rep. of Germany | 128/752 |
| 159394 | 3/1983 | Fed. Rep. of Germany | 128/754 |
| 149537 | 7/1961 | U.S.S.R. | 128/305 |

*Primary Examiner*—Edward M. Coven
*Assistant Examiner*—Max F. Hindenburg
*Attorney, Agent, or Firm*—Barnes, Kisselle, Raisch, Choate, Whittemore & Hulbert

[57] ABSTRACT

A biopsy needle for excising tissue specimens for microscopic examination including a tubular sheath having an axially extending open-side and a tapered point. The open side is provided with opposed grooves which guide a slidable stylet having a tapered end with sharp cutting edges. The tapered end of the stylet is either preformed to curve to the tapered point of the sheath or guided in internal grooves of the sheath to the insertion point of the sheath to occlude the tapered end of the sheath and incise and enclose a tissue specimen.

6 Claims, 11 Drawing Figures

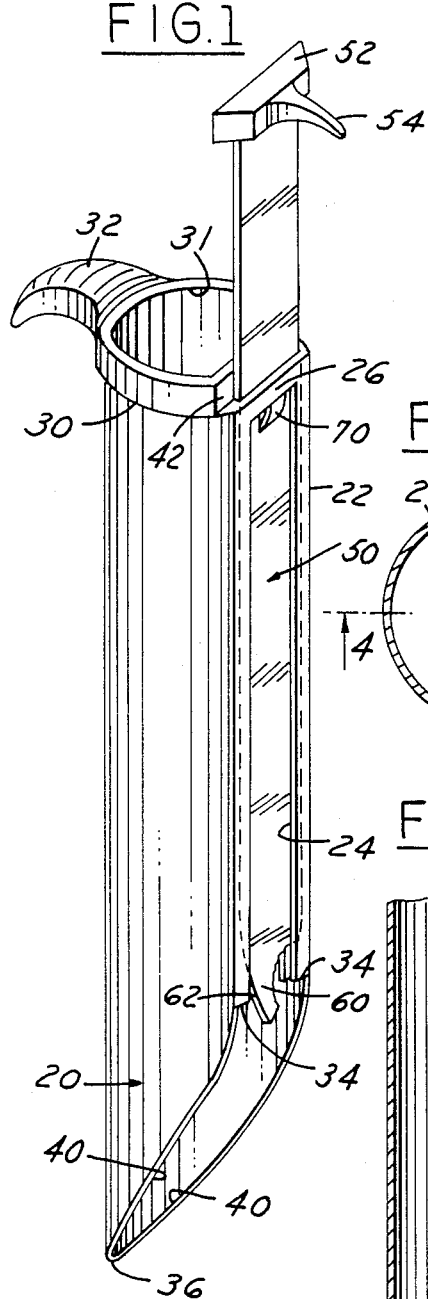
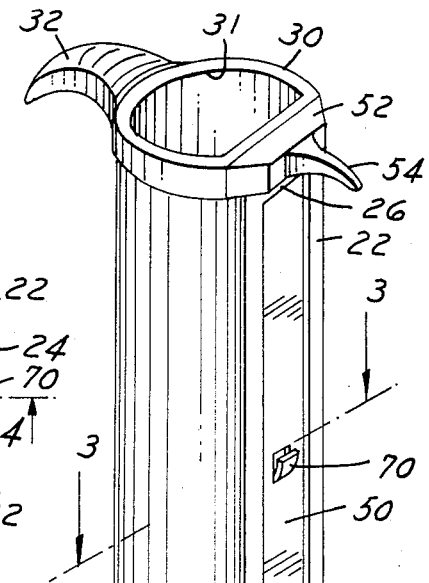
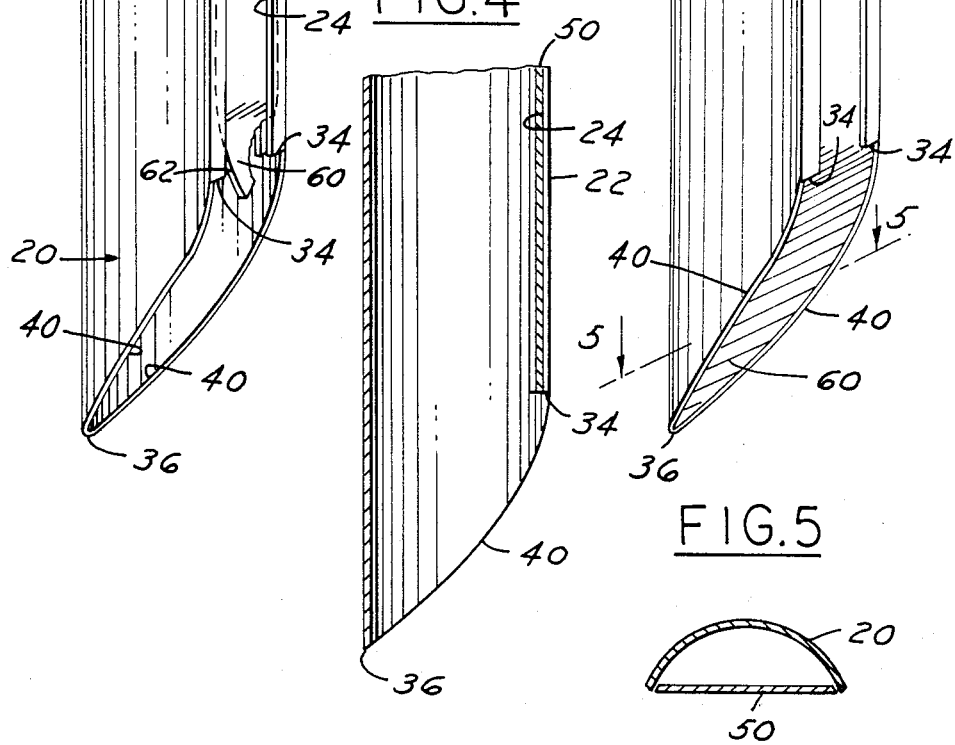
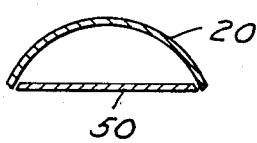

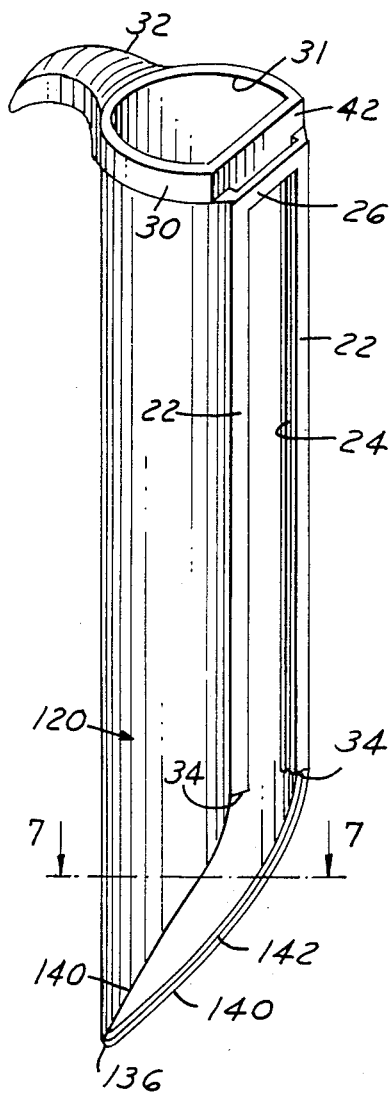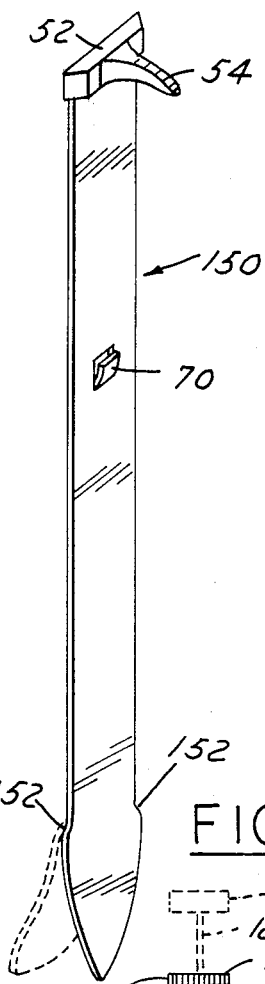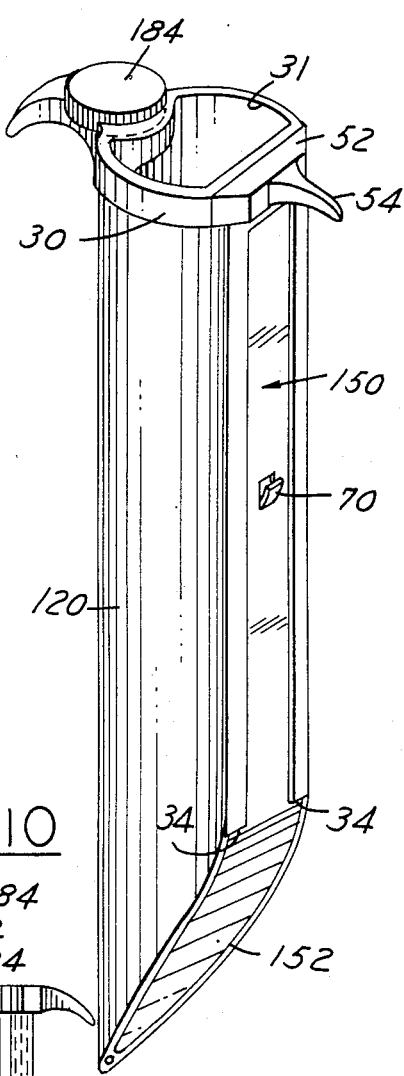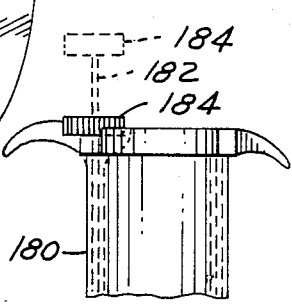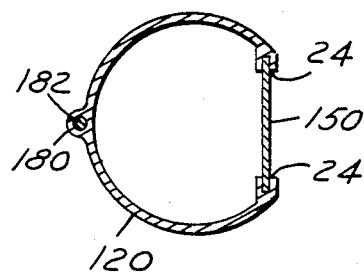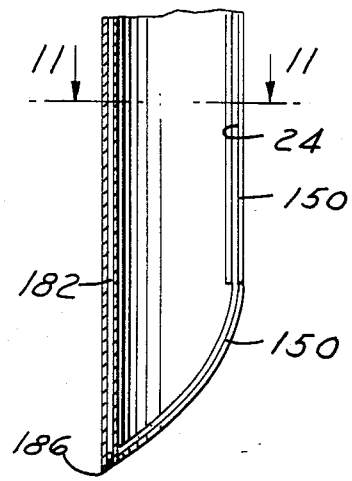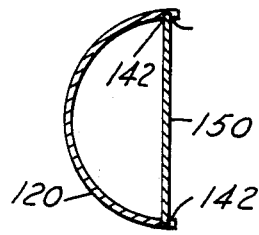

BIOPSY NEEDLE

FIELD OF INVENTION

Devices utilized by physicians and surgeons for excising small portions of living animal tissue for examination to determine the presence or absence of disease such as malignancy.

BACKGROUND AND OBJECTIVES OF THE INVENTION

In the present day practice of medicine, the alert physician is constantly watchful for tumors or other abnormal growth in the human body which may be malignant. Tumors do not respond to body mechanisms that limit growth. Unlike benign tumors, those which are malignant show an atypical cell structure with undifferentiated rather than functional specialized cells. These malignant cells have a characteristic of invasiveness of surrounding tissue. As a result, early detection is extremely important. Cancers discovered early before metastasis have the best cure rates. Tissue has to be obtained for classification, grading and staging of the disease.

Historically, the open surgical method was utilized for obtaining tissue specimens for examination. This required either local or, sometimes, general anesthesia as well as an incision which was expensive and also associated with more discomfort for the patient and a longer healing period.

The detection of malignancy is presently best determined by examination of an excised portion of the suspect tissue which is removed in the form of wedges or cylindrical pieces by an incursive instrument often referred to as a biopsy needle. Once the tissue specimen is obtained, it is fixed, i.e., killed and coagulated and chemical and histological analyses are carried out. In many instances, the analysis is performed very rapidly during an operation so that the surgeon has a guide to determine the extent of the corrective surgery.

It is desirable that tissue excision be done with as little injury to the surrounding tissue as possible. There are a number of biopsy procedures in use but none are entirely satisfactory. One type relies on suction applied by an attached syringe. This tears the tissue from its base and often fragments are obtained or the needle returns with no specimen. The type of needle which utilizes a cutting mechanism must replace the stylet (slender probe) with a cutting blade or blades and retrieval of the specimen is not always successful. Another type uses suction and a deflector for the blade to cut the tissue but by the very nature of this device the tissue distal to the deflector is lost.

Another type of needle uses a stylet with a partial diametric cut-out a short distance from the tip. This stylet is advanced into the tissue to be tested which is intended to bulge into the recess after which a sheath is brought down over the stylet cutting and trapping the specimen.

It is an object of the present invention to provide a biopsy needle to obtain a specimen which fills the entire volume of the provided recess in the needle sheath and which cuts the tissue clearly and retains it securely for safe retrieval.

It is, therefore, the objective to provide a biopsy needle in which the size of the retrieved specimen corresponds to the designed volume of the biopsy needle. This allows the use of smaller gauge needles to obtain the same quantity of tissue as with the larger types of needles above referenced.

A further object is the clean cutting of the tissue at the base of the incursion so there is no unnecessary incursion and no tearing of the tissue. As a consequence, there is no fragmentation or distortion of the specimen.

The needle is designed to isolate positively the specimen to be cut and is not dependent on an undependable bulging of the tissue. No suction is required in the operation of the needle to be described and no intraluminal stylet is needed.

Another advantage of the present invention is that multiple specimens may be obtained without the need to withdraw the needle.

Two patients which disclose biopsy needles are the U.S. Pat. No. 3,001,522, to Silverman, issued Sept. 26, 1961 and the U.S. Pat. No. 3,007,471, to McClure, Jr., issued Nov. 7, 1961. See also an article by John M, McClure, Jr. in *Surgery*, vol. 51, April. 1962, page 515. These patents disclose structures which utilize cutting blades for the tissue specimen but each leaves a quantity of tissue contained in the needle.

The most recent instrument used in biopsies is the very thin needle called the skinny needle, but this has the disadvantage that it delivers mostly cells and the interpretation of the sample requires special training and skill which is not always available. Even with highly trained technicians, there are cells which cannot be classified as benign or malignant unless they is a way to study their distribution in the tissue. The tiny specimens do not provide this information. With the "skinny needle" the ratio of the wall thickness to the lumen (the space enclosed by the tubular walls) favors the luman area. The total bulk of the needle is very fine.

With the present invention, the bulk of the biopsy needle can also be very fine. Briefly, my design incorporates a very fine, thin-walled needle in two parts, one of which encloses the major portion of the lumen and the other of which closes the lumen wall and acts as a trocar and cutting blade. A trocar is a stylet with a triangular point.

Other objects and features of the invention will be apparent in the following description and claims in which the invention is described together with details to enable persons skilled in the art to practice the invention, all in connection with the best mode presently contemplated for the invention.

BRIEF DESCRIPTION OF THE DRAWINGS

Drawings accompany the disclosure and the various views thereof may be briefly described as:

FIG. 1, a perspective elevation of a biopsy needle assembly constructed in accordance with the present invention.

FIG. 2, a view of the needle in closed position.

FIG. 3, a sectional view on line 3—3 of FIG. 2.

FIG. 4, a longitudinal section on line 4—4 of FIG. 3.

FIG. 5, a sectional view on line 5—5 of FIG. 2.

FIG. 6, a perspective elevation of a modified form of the invention.

FIG. 7, a sectional view on line 7—7 of FIG. 6.

FIG. 8, a view of a cutting blade removed from the needle.

FIG. 9, a perspective elevation of another modified form with a supplemental needle hub.

FIG. 10, a side elevation of the modification shown in FIG. 9.

FIG. 11, a sectional view on line 11—11 of FIG. 10.

DETAILED DESCRIPTION OF THE INVENTION AND THE MANNER AND PROCESS OF USING IT

With reference to the drawings, the biopsy needles depicted are shown rather short and thick to facilitate the disclosure of the detail required for a proper understanding of the invention. In actual practice, the needle would be quite thin, preferably in the range of 2 mm inner diameter, but could be varied to larger sizes as the conditions may call for.

In FIG. 1, the needle body 20 is cylindrical in shape with a flat open side with opposed edges 22 formed with opposed slots 24. The vertical edges are joined at the top by a bar 26. the open top of the body has a rim 30 in the form of a circular metal part with an opening 31 which fits over the top edge of the body. A finger projection 32 from the rim 30 facilitates handling of the needle. The top rim is referred to as a hub.

The opposed slots 24 terminate at the lower end at 34 and at this point the body tapers to the opposite side toward a point 36. The edges 40 of this tapered portion of the body are sharp tissue cutting edges.

On the rim 30 opposite the projection 32 is a flat closure piece 42 spaced inwardly of the bar 26 to provide an opening leading to and aligning with the slots 24.

A sliding closure and cutting wall stylet 50 is dimensioned laterally to slide in the slots 24. This stylet 50 is made of thin tempered steel. At the top end, as viewed in the drawings, is secured a hub block 52 with a manipulation projection 54. The other end 60 of the wall stylet has a tapered end which is preformed into a curve to complement the curved cutting edges 40 at the lower insertion end of the body 20. The point and side edges 62 of the tapered end of the wall stylet are formed with sharp cutting edges which will function as described below.

A stop 70 is struck from the wall stylet 50 spaced from the upper end. This stop will limit the retractive motion of the wall stylet by striking the bar 26. The wall stylet may be removed by pushing in the strike-out 70 while it passes the bar 26.

In the use of the above-described assembly depicted in FIGS. 1 to 5, the plate 50 is advanced into the sheath until both hubs 30 and 52 are level. In this position, the blade or wall stylet 50 occludes the bevel of the sheath 20. The needle body is then introduced into the flesh and when the perimeter of the tissue to be diagnosed is reached, the needle is opened by sliding the hub 52 up until stop 70 reaches the bar 26. This indicates that the insertion end of the sheath is open. The needle is now advanced into the tissue to the desired depth and the sheath isolates (sets up) the tissue for the cut. The hub 52 is then forced into the sheath and the cutting end of the wall stylet is moved to close the lower end of the sheath 20 with the movement of the curved end of the wall stylet. By this action, the tissue specimen is then cleanly separated from the host tissue and trapped in the sheath. The needle may now be withdrawn without tearing any tissue and leaving an unfractured area. FIG. 5 shows the blade 50 in a section at line 5—5 of FIG. 2.

When using the needle with one hand only, while the other hand fixes a tumor, for example, located in the breast, the following procedure can be followed. The needle is best held between the index finger placed under the hub 52, 54 of the wall stylet 50 and the middle finger under the hub 30, 32 of the sheath 20 while the thumb rests on the hub of the sheath. When the perimeter of the area to be diagnosed is reached, the hub of the wall stylet is retracted until the stop 70 reaches the bar 26. The needle is now advanced into the respective tissue to the desired depth. While the needle is held steady with the index and ring finger, the thumb pushes the hub 52 of the wall stylet into the closed position. The desired specimen is thus cut and stored in the sheath.

FIGS. 6, 7 and 8 illustrate a modification of the invention in which like parts carry reference characters of FIGS. 1 to 5. In this embodiment, the body 120 differs from that of FIG. 1 in that the lower cutting edges 140 have grooves 142 on the inside wall to receive and guide the cutting blade 150 which again is formed of tempered steel. This blade is slightly widened at 152 to dimension which will be readily received in the slots 24 but which will engage the shallow grooves 142 and guide the flexible blade along the curved end of the body to the tip 136. In FIG. 8, the dotted lines indicate the final closed position of the blade.

This embodiment will function in the same manner as that described in connection with FIGS. 1 to 5.

If more than one specimen is required, the same sequence as described above can be repeated without need of withdrawal of the needle from the body or organ. The specimens will be stacked neatly within the sheath. After withdrawal of the assembly, the wall stylet can be withdrawn from the sheath by depressing the strike-out. The various specimens can then be readily identified and removed.

In FIGS. 9, 10 and 11, a structure is shown similar to that described in connection with FIGS. 6, 7 and 8 with the exception that a stylet or needle lumen is formed by an elongate tubular appendage 180 along the outer wall of the body 120. A needle 182 is insertable in this lumen having a knurled hub 184. This stylet and the lumen are preferably beveled at 186 toward the point of the sheath to provide a supplementary point for easy penetration of tissue. The hub 184 allows the stylet to be easily grapsed for the insertion and removal. After a biopsy has been taken and the specimen is securely locked in the sheath, the laterally extending hub 184 of stylet 182 can be grasped and the stylet removed and an agent injected without making contact with the biopsy specimen.

It will thus be seen that the biopsy needle described can be formed in slender dimensions and with desired lengths for various biopsies as required. The combination of the open-sided sheath (U-shaped) sheath with the cutting wall blade or stylet which closes the sheath and which occludes or opens the beveled insertion end of the sheath provides a clean cut of the desired tissue and encloses specimens for withdrawal. The design permits larger specimens to be obtained with a relatively small gauge needle and also allows multiple specimens to be obtained without withdrawal.

What is claimed is:

1. A biopsy needle for penetrating, cutting and removing tissue specimens which comprises:
    (a) a sheath having a hub end and an insertion end and in the form of an open-wall tube essentially U-shaped in cross-section having laterally opposed edges at the open side extending from the hub end to the insertion end of the sheath, and a taper formed at the insertion end, said sheath being open at both the hub end and the insertion end with a passageway therebetween, (b) an elongate cutting wall stylet having a sharpened insertion end and shaped to cut an included specimen and close the open side of said sheath, and (c) means to guide said stylet in a longitudinal sliding motion along the laterally opposed edges of said sheath from the hub end to the insertion end and vice versa wherein said insertion end of said stylet may open or occlude said insertion end of said sheath.

2. A biopsy needle as defined in claim 1 in which said means to guide said stylet comprises guiding grooves formed in said opposed edges.

3. A biopsy needle as defined in claim 1 in which said means to guide said stylet comprises slots formed in said opposed edges and grooves below said slots on the inside of the wall of said sheath at the tapered end to guide the insertion end of the stylet to an occluding position.

4. A biopsy needle as defined in claim 1 in which said cutting wall stylet is formed of tempered metal having a curve at the insertion end to complement the tapered end of said sheath.

5. A biopsy needle as defined in claim 1 in which a stylet lumen is provided longitudinally along said sheath independent of the passageway in said sheath, and a stylet in said lumen sharpened to complement said tapered insertion end of said sheath, said lumen serving for the administration of fluid agents during insertion of said needle into specified tissue.

6. A biopsy needle for penetrating, cutting and removing tissue specimens which comprises:

(a) a sheath having a hub end and an insertion end and in the form of an open-wall tube essentially U-shaped in cross-section having laterally opposed edges at the open side extending from the hub end to the insertion end of the sheath, and a taper formed at the insertion end, said sheath being open at both the hub end and the insertion end with a passageway therebetween, (b) an elongate cutting wall stylet having a sharpened insertion end and shaped to cut an included specimen and close the open side of said sheath, and (c) means to guide said stylet in a longitudinal sliding motion along the laterally opposed edges of said sheath from the hub end to the insertion end and vice versa wherein said insertion end of said stylet may open or occlude said insertion end of said sheath, (d) said sheath having a hub ring formed at the hub end with a lateral bar at the top of the open side providing a guide slot for said stylet, and (e) a flexible strike-out formed in said stylet to serve as a retraction stop in cooperation with said lateral bar to limit the retraction of said stylet from said sheath, said strike-out being manually displaceable to allow said stylet to be slideably removed from said sheath.

* * * * *